United States Patent [19]
Dankworth et al.

[11] Patent Number: 5,650,536
[45] Date of Patent: Jul. 22, 1997

[54] CONTINUOUS PROCESS FOR PRODUCTION OF FUNCTIONALIZED OLEFINS

[75] Inventors: David C. Dankworth, Whitehouse Station; William H. Cross, Roselle; Joseph V. Cusumano, Watchung; William D. Diana, Belle Mead; William B. Eckstrom, Fanwood, all of N.J.; Jacob I. Emert, Brooklyn, N.Y.; Keith R. Gorda, Little York, N.J.; Robert M. Koros, Westfield, N.J.; Harold W. Margo, Colonia, N.J.; Jon E. Stanat, Westfield, N.J.

[73] Assignee: Exxon Chemical Patents Inc., Linden, N.J.

[21] Appl. No.: 261,560

[22] Filed: Jun. 17, 1994

Related U.S. Application Data

[63] Continuation-in-part of Ser. No. 992,403, Dec. 17, 1992, abandoned.

[51] Int. Cl.$^6$ .................................................. C07C 67/00
[52] U.S. Cl. .......................... 560/204; 560/193; 560/233
[58] Field of Search .................................... 560/233, 204, 560/193, 201

[56] References Cited

U.S. PATENT DOCUMENTS

| | | | |
|---|---|---|---|
| Re. 26,433 | 8/1968 | Le Suer | 252/33.6 |
| 2,586,070 | 2/1952 | Luten, Jr. et al. | 260/624 |
| 2,831,877 | 4/1958 | Koch | 260/413 |

(List continued on next page.)

FOREIGN PATENT DOCUMENTS

| | | | |
|---|---|---|---|
| 1319703 | 6/1993 | Canada | C07C 51/14 |
| 0129368A1 | 12/1984 | European Pat. Off. | |
| 148592 | 7/1985 | European Pat. Off. | C08F 8/00 |
| 0148592A2 | 7/1985 | European Pat. Off. | |
| 313150 | 4/1989 | European Pat. Off. | C08C 19/00 |
| 0310878A1 | 4/1989 | European Pat. Off. | C07C 53/124 |
| 0397276 | 11/1990 | European Pat. Off. | |
| 397276 | 11/1990 | European Pat. Off. | C08C 19/00 |
| 0462319A1 | 12/1991 | European Pat. Off. | |
| 2101485 | 3/1972 | France | |
| 62-164645 | 1/1986 | Japan | |
| 62-192338 | 2/1986 | Japan | |
| 4-15240 | 5/1990 | Japan | |
| 51-41320 | 5/1990 | Japan | |
| 984409 | 2/1965 | United Kingdom | |
| 1085903 | 4/1967 | United Kingdom | |
| 1162436 | 8/1969 | United Kingdom | |
| 1188900 | 4/1970 | United Kingdom | |
| 1223660 | 3/1971 | United Kingdom | |
| 1343447 | 1/1974 | United Kingdom | |
| 1422308 | 1/1976 | United Kingdom | |
| WO94/13709 | 6/1994 | WIPO | C08F 8/00 |

OTHER PUBLICATIONS

Billmeyer, J.R., Textbook of Polymer Sciences, 2nd Edition, J. Wiley, pp. 3–21 (1971).

N. Bahrmann, Chapter 5, Koch Reactions, "New Syntheses with Carbon Monoxide", Edited by J. Falbe; Springer-Verlag, New York, New York 1980.

Y. Komatsu et al., Maruzen Sekiyo Gihi 21, 51 (1976).

Ya Eidus et al., "Synthesis of Derivatives of Carboxylic Acids Under Acid Catalysis Conditions from Carbon Monoxide, Olefins, and Compounds being Acylated" Z. Org. Chem. 4(3) 376 (1968).

Gushcin, et al., "Investigation of the Reaction of Ozone with Phenols", Neftekhimiya, vol. 12, (No. 3) 383 (1972).

(List continued on next page.)

*Primary Examiner*—Samuel Barts
*Attorney, Agent, or Firm*—K. R. Walton; J. F. Hunt

[57] ABSTRACT

A continuous process for functionalizing olefins, especially polymer olefins in a CSTR or pipe reactor. Esters are preferably produced by continuous reaction of the olefin with carbon monoxide and a nucleophilic trapping agent. The liquid-filled pipe reactor operates in plug flow with static mixers and the CSTR is operated in the substantial absence of air at constant liquid level.

29 Claims, 1 Drawing Sheet

U.S. PATENT DOCUMENTS

| | | | |
|---|---|---|---|
| 2,967,873 | 1/1961 | Koch et al. | 260/410.9 |
| 3,005,846 | 10/1961 | Friedman et al. | 260/497 |
| 3,036,003 | 5/1962 | Verdol | 252/33.4 |
| 3,059,007 | 10/1962 | Vos et al. | 260/413 |
| 3,068,256 | 12/1962 | Roming, Jr. | 260/413 |
| 3,087,936 | 4/1963 | Le Suer | 260/326.3 |
| 3,135,716 | 6/1964 | Uraneck et al. | 260/45.5 |
| 3,167,585 | 1/1965 | Anderson et al. | 260/533 |
| 3,184,411 | 5/1965 | Lowe | 252/46.7 |
| 3,185,645 | 5/1965 | Clayton | 252/46.7 |
| 3,185,704 | 5/1965 | Kahn et al. | 260/326.3 |
| 3,200,107 | 8/1965 | Le Suer | 260/132 |
| 3,245,908 | 4/1966 | Lowe | 252/51.5 |
| 3,245,909 | 4/1966 | Lowe | 252/51.5 |
| 3,245,910 | 4/1966 | Lowe | 252/51.5 |
| 3,254,025 | 5/1966 | Le Suer | 252/32.7 |
| 3,256,185 | 6/1966 | Le Suer | 252/32.7 |
| 3,278,550 | 10/1966 | Norman et al. | 260/326.3 |
| 3,280,034 | 10/1966 | Anzenberger et al. | 252/51.5 |
| 3,281,428 | 10/1966 | Le Suer | 260/326.3 |
| 3,282,955 | 11/1966 | Le Suer | 260/326.3 |
| 3,284,410 | 11/1966 | Meinhardt | 252/49.6 |
| 3,306,908 | 2/1967 | Le Suer | 260/326.3 |
| 3,312,619 | 4/1967 | Vineyard | 252/47.5 |
| 3,331,776 | 7/1967 | Krukziener | 252/56 |
| 3,338,832 | 8/1967 | Le Suer | 252/47.5 |
| 3,344,069 | 9/1967 | Stuebe | 252/49.6 |
| 3,349,107 | 10/1967 | Pawlenko | 260/410.9 |
| 3,361,673 | 1/1968 | Stuart et al. | 252/51.5 |
| 3,366,569 | 1/1968 | Norman et al. | 252/51.5 |
| 3,367,943 | 2/1968 | Miller et al. | 260/326.3 |
| 3,369,021 | 2/1968 | Le Suer | 260/268 |
| 3,373,111 | 3/1968 | Le Suer et al. | 252/51.5 |
| 3,381,022 | 4/1968 | Le Suer | 260/404.8 |
| 3,390,086 | 6/1968 | O'Halloran | 252/47.5 |
| 3,401,118 | 9/1968 | Benoit, Jr. | 252/51.5 |
| 3,403,102 | 9/1968 | Le Suer | 252/49.8 |
| 3,415,750 | 12/1968 | Anzenberger | 252/51.5 |
| 3,428,561 | 2/1969 | Le Suer | 252/32.5 |
| 3,442,808 | 5/1969 | Traise et al. | 252/49.6 |
| 3,445,441 | 5/1969 | Rushton | 260/89.5 |
| 3,455,832 | 7/1969 | Davis | 252/51.5 |
| 3,458,530 | 7/1969 | Siegel et al. | 260/326.5 |
| 3,470,098 | 9/1969 | O'Halloran | 252/47.5 |
| 3,493,520 | 2/1970 | Verdol et al. | 252/51.5 |
| 3,502,677 | 3/1970 | Le Suer | 260/268 |
| 3,513,093 | 5/1970 | Le Suer | 252/32.5 |
| 3,522,179 | 7/1970 | Le Suer | 252/51.5 |
| 3,527,779 | 9/1970 | Paulis et al. | 260/413 |
| 3,533,945 | 10/1970 | Vogel | 252/49.6 |
| 3,539,633 | 11/1970 | Piasek et al. | 260/570.5 |
| 3,539,654 | 11/1970 | Pautrat et al. | 260/768 |
| 3,541,012 | 11/1970 | Stuebe | 252/51.5 |
| 3,542,680 | 11/1970 | Le Suer | 252/57 |
| 3,551,466 | 12/1970 | Gee et al. | 260/429 |
| 3,558,743 | 1/1971 | Verdol et al. | 260/848 |
| 3,573,205 | 3/1971 | Lowe et al. | 252/51.5 |
| 3,579,450 | 5/1971 | Le Suer | 252/56 |
| 3,595,942 | 7/1971 | Wald et al. | 260/880 |
| 3,600,372 | 8/1971 | Udelbefon | 260/132 |
| 3,639,242 | 2/1972 | Le Suer | 252/56 R |
| 3,649,659 | 3/1972 | Otto et al. | 260/429 R |
| 3,652,616 | 3/1972 | Watson et al. | 260/429 R |
| 3,681,415 | 8/1972 | Schell | 260/410.9 R |
| 3,692,681 | 9/1972 | Liston | 252/51.5 A |
| 3,697,428 | 10/1972 | Meinhardt et al. | 252/56 D |
| 3,703,536 | 11/1972 | Piasek et al. | 260/462 R |
| 3,708,522 | 1/1973 | Le Suer | 260/485 G |
| 3,711,406 | 1/1973 | Lowe | 252/33.4 |
| 3,715,313 | 2/1973 | Haseltine et al. | 252/52 |
| 3,718,663 | 2/1973 | Piasek et al. | 260/326.3 |
| 3,749,695 | 7/1973 | de Vries | 252/47.5 |
| 3,755,169 | 8/1973 | Adams et al. | 252/35 |
| 3,795,615 | 3/1974 | Pappas et al. | 252/59 |
| 3,803,087 | 4/1974 | Vaughn | 260/47 |
| 3,859,318 | 1/1975 | Le Suer | 260/410.6 |
| 3,865,740 | 2/1975 | Goldschmidt | 252/46.7 |
| 3,865,813 | 2/1975 | Gergel | 260/239.3 R |
| 3,870,734 | 3/1975 | Onopchenko et al. | 260/413 |
| 3,903,003 | 9/1975 | Murphy et al. | 252/51.5 A |
| 3,910,963 | 10/1975 | Souma et al. | 260/343 |
| 3,954,639 | 5/1976 | Liston | 252/47.5 |
| 3,992,423 | 11/1976 | Massie | 260/410.6 |
| 4,073,737 | 2/1978 | Elliott | 252/51.5 A |
| 4,102,798 | 7/1978 | Ryer et al. | 252/51.5 A |
| 4,108,945 | 8/1978 | Fetters et al. | 260/880 B |
| 4,113,639 | 9/1978 | Lonstrup et al. | 252/51.5 A |
| 4,116,876 | 9/1978 | Brois et al. | 252/49.6 |
| 4,156,128 | 5/1979 | Craven | 219/523 |
| 4,224,232 | 9/1980 | Onopchenko et al. | 260/413 |
| 4,234,435 | 11/1980 | Meinhardt et al. | 252/51.5 A |
| 4,250,240 | 2/1981 | Petersen | 528/14 |
| 4,256,913 | 3/1981 | Jung et al. | 562/521 |
| 4,262,138 | 4/1981 | Gelbein | 560/233 |
| 4,312,965 | 1/1982 | Jachimowicz et al. | 525/378 |
| 4,323,698 | 4/1982 | Haag et al. | 560/233 |
| 4,518,798 | 5/1985 | Kramer et al. | 560/233 |
| 4,539,654 | 9/1985 | Deyer | 364/900 |
| 4,611,086 | 9/1986 | Gueguen et al. | 568/897 |
| 4,665,174 | 5/1987 | Minai et al. | 544/59 |
| 4,668,834 | 5/1987 | Rim et al. | 585/12 |
| 4,681,707 | 7/1987 | Alper et al. | 260/410.9 R |
| 4,704,427 | 11/1987 | Kitahara et al. | 524/531 |
| 4,717,755 | 1/1988 | Doi et al. | 525/333.7 |
| 4,789,714 | 12/1988 | Cozewith et al. | 526/88 |
| 4,797,219 | 1/1989 | Gutierrez et al. | 252/56 D |
| 4,798,873 | 1/1989 | Meurer et al. | 525/333.7 |
| 4,857,217 | 8/1989 | Gutierrez et al. | 252/47 |
| 4,866,135 | 9/1989 | Gutierrez et al. | 525/285 |
| 4,866,139 | 9/1989 | Gutierrez et al. | 525/333.7 |
| 4,866,140 | 9/1989 | Gutierrez et al. | 525/333.7 |
| 4,866,141 | 9/1989 | Gutierrez et al. | 525/333.7 |
| 4,866,142 | 9/1989 | Gutierrez et al. | 525/333.7 |
| 4,902,822 | 2/1990 | Drent | 560/233 |
| 4,906,394 | 3/1990 | Gutierrez et al. | 252/51.5 A |
| 4,927,892 | 5/1990 | Drent et al. | 525/340 |
| 4,929,689 | 5/1990 | Meurer et al. | 525/333.9 |
| 4,952,739 | 8/1990 | Chen | 585/18 |
| 4,956,107 | 9/1990 | Gutierrez et al. | 252/47 |
| 4,963,275 | 10/1990 | Gutierrez et al. | 252/47 |
| 4,980,422 | 12/1990 | Willis | 525/370 |
| 5,017,199 | 5/1991 | Etchepare | 55/57 |
| 5,017,299 | 5/1991 | Gutierrez et al. | 252/51.5 R |
| 5,049,294 | 9/1991 | Van Zon et al. | 252/51.5 A |
| 5,070,131 | 12/1991 | Rhodes et al. | 524/484 |
| 5,084,534 | 1/1992 | Welborn, Jr. et al. | 526/160 |
| 5,102,566 | 4/1992 | Fetterman, Jr. et al. | 252/32.7 E |
| 5,229,022 | 7/1993 | Sing et al. | 256/56 |
| 5,235,067 | 8/1993 | Allen et al. | 548/520 |

OTHER PUBLICATIONS

Wender, I., Organic Synthesis via Metal Carbonyls, vol. 2, pp. 233–296, 1980.

Puzitskii et al., *Carbonylation of Olefins and Alcohols with Carbon Monoxide in the Presence of a Catalyst System: $BF_3H_2O$–Liquid $SO_2$.* Izvestiya Akademii Nauk SSSR, Seriya Khimicheskaya, No. 10, pp. 2331–2334, Oct. 1977.

Chemical Abstracts No. CA77 (12):76298p, 1977.

Chemischer Informationdienst 41 (1972).

CONTINUOUS PROCESS FOR PRODUCTION OF FUNCTIONALIZED OLEFINS

CROSS REFERENCE

This application is a continuation-in-part of U.S. Ser. No. 992,403 for "Polymers Functionalized By Koch Reaction and Derivatives Thereof" filed Dec. 17, 1992, now abandoned in favor of continuing application U.S. Ser. No. 08/534,891, filed Sep. 25, 1995.

BACKGROUND OF THE INVENTION

The present invention is directed to continuous production of functionalized olefins, more particularly by continuously reacting polymeric olefins with carbon monoxide and a functionalizing agent, in the presence of acid catalyst to produce carboxylated olefins such as polymeric esters.

The present invention is directed to an improved polymer functionalized by the Koch reaction more particularly by reacting at least one carbon-carbon double bond with carbon monoxide in the presence of an acidic catalyst and a nucleophilic trapping agent to form a carbonyl or thiocarbonyl functional group, and derivatives thereof.

The term "polymer" is used herein to refer to materials comprising large molecules built up by the repetition of small, simple chemical units. In a hydrocarbon polymer those units are predominantly formed of hydrogen and carbon. Polymers are defined by average properties, and in the context of the invention polymers have a number average molecular weight (Mn) of at least 500. The term "hydrocarbon" is used above herein to refer to non polymeric compounds comprising hydrogen and carbon having uniform properties such as molecular weight. However, the term "hydrocarbon" is not intended to exclude mixtures of such compounds which individually are characterized by such uniform properties.

Both hydrocarbon compounds as well as polymeric compounds have been reacted to form carboxyl group-containing compounds and their derivatives. Carboxyl groups have the general formula —CO—OR, where R can be H, a hydrocarbyl group, or a substituted hydrocarbyl group. The synthesis of carboxyl group-containing compounds from olefinic hydrocarbon compounds, carbon monoxide, and water in the presence of metal carboxyls is disclosed in references such as N. Bahrmann, Chapter 5, Koch Reactions, "New Synthesis with Carbon Monoxide" J. Falbe; Springer-Verlag, New York, 1980. Hydrocarbons having olefinic double bonds react in two steps to form carboxylic acid-containing compounds. In the first step an olefin compound reacts with an acid catalyst and carbon monoxide in the absence of water. This is followed by a second step in which the intermediate formed during the first step undergoes hydrolysis or alcoholysis to form a carboxylic acid or ester. An advantage of the Koch reaction is that it can occur at moderate temperatures of −20° C. to +80° C., and pressures up to 100 bar.

The Koch reaction can occur at double bonds where at least one carbon of the double bond is di-substituted to form a "neo" acid or ester

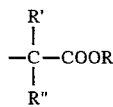

(where R' and R" are not hydrogen)

The Koch reaction can also occur when both carbons are mono-substituted or one is monosubstituted and one is unsubstituted to form an "iso" acid (i.e. -R'HC—COOR). Bahrmann et al. discloses isobutylene converted to isobutyric acid via a Koch-type reaction. U.S. Pat. No. 2,831,877 discloses a multi-phase, acid catalyzed, two-step process for the carboxylation of olefins with carbon monoxide. Complexes of mineral acids in water with $BF_3$ have been studied to carboxylate olefins. U.S. Pat. No. 3,349,107 discloses processes which use less than a stoichiometric amount of acid as a catalyst. Examples of such complexes are $H_2O.BF_3.H_2O$, $H_3PO_4.BF_3.H_2O$ and $HF.BF_3.H_2O$.

EP-A-0148592 relates to the production of carboxylic acid esters and/or carboxylic acids by catalyzed reaction of a polymer having carbon-carbon double bonds, carbon monoxide and either water or an alcohol, optionally in the presence of oxygen. The catalysts are metals such as palladium, rhodium, ruthenium, iridium, and cobalt in combination with a copper compound, in the presence of a protonic acid such as hydrochloric acid. A preferred polymer is polyisobutene, which may have at least 80% of its carbon-carbon double bonds in the form of terminal double bonds. Liquid polyisobutene having a number average molecular weight in the range of from 200 to 2,500, preferably up to 1,000 are described.

U.S. Pat. No. 4,927,892 relates to reacting a polymer or copolymer of a conjugated diene, at least part of which is formed by 1,2 polymerization, with carbon monoxide and water and/or alcohol in the presence of a catalyst prepared by combining a palladium compound, certain ligands and/or acid except hydrohalogenic acids having a pKa of less than 2. Useful Lewis acids include $BF_3$.

U.S. Pat. No. 5,235,067 discloses continuous acylation of alkenyl-substituted mono- and bis-succinimides and their Mannich coupled intermediates but functionalization of an olefin is not shown.

Although there are disclosures in the art of olefinic hydrocarbons functionalized at the carbon-carbon double bond to form a carboxylic acid or derivative thereof via Koch-type chemistry, there is no disclosure that polymers containing carbon-carbon double bonds, including terminal olefinic bonds, either secondary or tertiary type olefinic bonds, could be successfully reacted via the Koch mechanism. Additionally, it has been found that the process of the present invention is particularly useful to make neo acid and neo ester functionalized polymer. Known catalysts used to carboxylate low molecular weight olefinic hydrocarbons by the Koch mechanism were found to be unsuitable for use with polymeric material. Specific catalysts have been found which can result in the formation of a carboxylic acid or ester at a carbon-carbon double bond of a polymer. Koch chemistry affords the advantage of the use of moderate temperatures and pressures, by using highly acidic catalysts and/or careful control of concentrations.

SUMMARY OF THE INVENTION

The present invention is a process for producing a functionalized polymer comprising continuously reacting a polymeric olefin and a gaseous functionalizing agent and recovering functionalized polymer. The present invention is also a continuous functionalization process comprising reacting an olefin with carbon monoxide and a nucleophilic trapping agent in the presence of an acid catalyst. The present invention is also a continuous process for producing carboxylated polymeric olefins comprising reacting said olefin with carbon monoxide and nucleophilic trapping agent in the presence of an acid catalyst in a substantially liquid-filled pipe reactor, preferably operated in laminar flow and recovering carboxylated polymer.

The present invention relates to a functionalized hydrocarbon polymer wherein the polymer backbone has $Mn \geq 500$, functionalization is by groups of the formula:

—CO—Y—R$^3$ wherein Y is O or S, and either R$^3$ is H, hydrocarbyl and at least 50 mole % of the functional groups are attached to a tertiary carbon atom of the polymer backbone, or R$^3$ is aryl, substituted aryl or substituted hydrocarbyl.

Thus the functionalized polymer may be depicted by the formula:

POLY-(CR$^1$R$^2$—CO—Y—R$^3$)$_n$     (I)

wherein POLY is a hydrocarbon polymer backbone having a number average molecular weight of at least 500, n is a number greater than 0, R$^1$, R$^2$ and R$^3$ may be the same or different and are each H, hydrocarbyl with the proviso that either R$^1$ and R$^2$ are selected such that at least 50 mole % of the —CR$^1$R$^2$ groups wherein both R$^1$ and R$^2$ are not H, or R$^3$ is aryl substituted aryl or substituted hydrocarbyl.

The present invention is also a gas-liquid pipe reactor process operated in laminar flow with Reynolds number less than 10 and including passing the reaction mass through a static mixer to disperse gas into liquid for reaction.

As used herein the term "hydrocarbyl" denotes a group having a carbon atom directly attached to the remainder of the molecule and having predominantly hydrocarbon character within the context of this invention and includes polymeric hydrocarbyl radicals. Such radicals include the following:

(1) Hydrocarbon groups; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, the two indicated substituents may together form a cyclic radical). Such radicals are known to those skilled in the art; examples include methyl, ethyl, butyl, hexyl, octyl, decyl, dodecyl, tetradecyl, octadecyl, eicosyl, cyclohexyl, phenyl and naphthyl (all isomers being included).

(2) Substituted hydrocarbon groups; that is, radicals containing non-hydrocarbon substituents which, in the context of this invention, do not alter predominantly hydrocarbon character of the radical. Those skilled in the art will be aware of suitable substituents (e.g., halo, hydroxy, alkoxy, carbalkoxy, nitro, alkylsulfoxy).

(3) Hetero groups; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen particularly non-basic nitrogen which would not deactivate the Koch catalyst, oxygen and sulfur.

In general, no more than about three substituents or hetero atoms, and preferably no more than one, will be present for each 10 carbon atoms in the hydrocarbon-based radical. Polymeric hydrocarbyl radicals are those derived from hydrocarbon polymers, which may be substituted and/or contain hetero atoms provided that they remain predominantly hydrocarbon in character. The functionalized polymer may be derived from a hydrocarbon polymer comprising non-aromatic carbon-carbon double bond, also referred to as an olefinically unsaturated bond, or an ethylenic double bond. The polymer is functionalized at that double bond via a Koch reaction to form the carboxylic acid, carboxylic ester or thio acid or thio ester.

Koch reactions have not heretofore been applied to polymers having number average molecular weights greater than 500. The hydrocarbon polymer preferably has Mn greater than 1,000. In the Koch process a polymer having at least one ethylenic double bond is contacted with an acid catalyst and carbon monoxide in the presence of a nucleophilic trapping agent such as water or alcohol. The catalyst is preferably a classical Broensted acid or Lewis acid catalyst. These catalysts are distinguishable from the transition metal catalysts of the type described in the prior art. The Koch reaction, as applied in the process of the present invention, may result in good yields of functionalized polymer, even 90 mole % or greater.

POLY, in general formula I, represents a hydrocarbon polymer backbone having Mn of at least 500. Mn may be determined by available techniques such as gel permeation chromatography (GPC). POLY is derived from unsaturated polymer.

DESCRIPTION OF THE PREFERRED EMBODIMENTS

Figure 1:
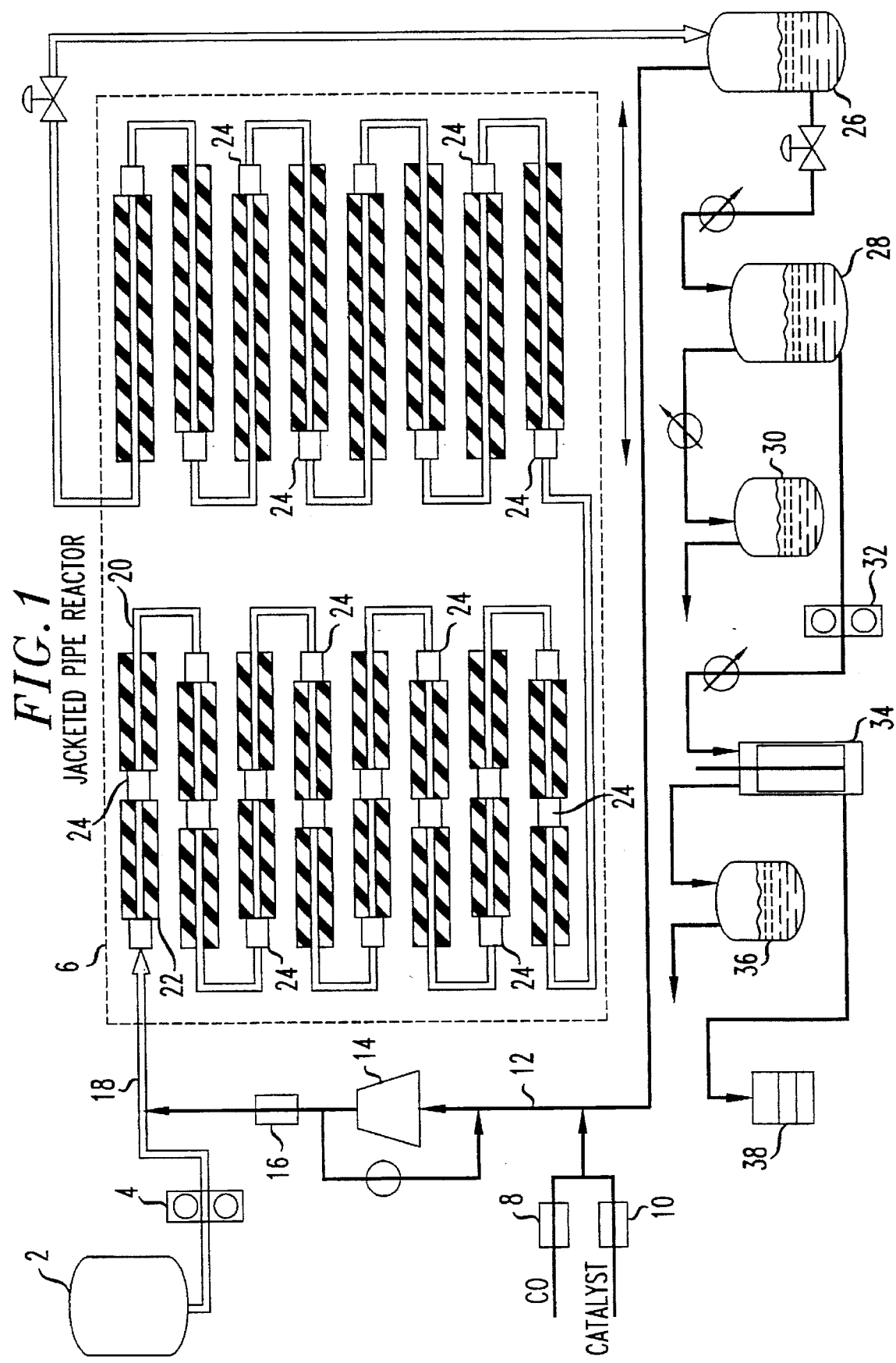
FIG. 1 is a schematic view of a jacketed pipe reactor with reagent supply, product recovery, and gas recycle means.

Olefins are useful in the process of the present invention. The olefinic unsaturation may be functionalized as described below for polymers. Useful olefins for oil additive applications include lower olefin materials, middle olefins such as $C_{18}$ olefins and polymeric olefins as described below. All olefins are susceptible to the invention so long as they operate in the improved continuous process of the invention to functionalize the olefinic unsaturation.

The polymers which are useful in the present invention are polymers containing at least one carbon-carbon double bond (olefinic or ethylenic) unsaturation. Thus, the maximum number of functional groups per polymer chain is limited by the number of double bonds per chain. Such polymers have been found to be receptive to Koch mechanisms to form carboxylic acids or derivatives thereof, using the catalysts and nucleophilic trapping agents of the present invention.

Useful polymers in the present invention include polyalkenes including homopolymer, copolymer (used interchangeably with interpolymer) and mixtures. Homopolymers and interpolymers include those derived from polymerizable olefin monomers of 2 to about 16 carbon atoms; usually 2 to about 6 carbon atoms.

Particular reference is made to the alpha olefin polymers made using organo metallic coordination compounds. A particularly preferred class of polymers are ethylene alpha olefin copolymers such as those disclosed in U.S. Pat. No. 5,017,299. The polymer unsaturation can be terminal, internal or both. Preferred polymers have terminal unsaturation, preferably a high degree of terminal unsaturation. Terminal unsaturation is the unsaturation provided by the last monomer unit located in the polymer. The unsaturation can be located anywhere in this terminal monomer unit. Terminal olefinic groups include vinylidene unsaturation, $R^aR^bC=CH^2$; trisubstituted olefin unsaturation, $R^aR^bC=CR^cH$; vinyl unsaturation, $R^aHC=CH_2$; 1,2-disubstituted terminal unsaturation, $R^aHC=CHR^b$; and tetra-substituted terminal unsaturation, $R^aR^bC=CR^cR^d$. At least one of $R^a$ and $R^b$ is a polymeric group of the present invention, and the remaining $R^b$, $R^c$ and $R^d$ are hydrocarbon groups as defined with respect to R, $R^1$, $R^2$, and $R^3$ above.

Low molecular weight polymers, also referred to herein as dispersant range molecular weight polymers, are polymers having Mn less than 20,000, preferably 500 to 20,000 (e.g. 1,000 to 20,000), more preferably 1,500 to 10,000 (e.g. 2,000 to 8,000) and most preferably from 1,500 to 5,000. The number average molecular weights are measured by vapor phase osmometry. Low molecular weight polymers are useful in forming dispersants for lubricant additives. Medium molecular weight polymers Mn's ranging from 20,000 to 200,000, preferably 25,000 to 100,000; and more preferably, from 25,000 to 80,000 are useful for viscosity index improvers for lubricating oil compositions, adhesive coatings, tackifiers and sealants. The medium Mn can be determined by membrane osmometry.

The higher molecular weight materials have Mn of greater than about 200,000 and can range to 15,000,000 with specific embodiments of 300,000 to 10,000,000 and more specifically 500,000 to 2,000,000. These polymers are useful in polymeric compositions and blends including elastomeric compositions. Higher molecular weight materials having Mn's of from 20,000 to 15,000,000 can be measured by gel permeation chromatography with universal calibration, or by light scattering. The values of the ratio Mw/Mn, referred to as molecular weight distribution, (MWD) are not critical. However, a typical minimum Mw/Mn value of about 1.1–2.0 is preferred with typical ranges of about 1.1 up to about 4.

The olefin monomers are preferably polymerizable terminal olefins; that is, olefins characterized by the presence in their structure of the group $-R-C=CH^2$, where R is H or a hydrocarbon group. However, polymerizable internal olefin monomers (sometimes referred to in the patent literature as medial olefins) characterized by the presence within their structure of the group:

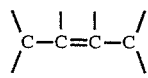

can also be used to form the polyalkenes. When internal olefin monomers are employed, they normally will be employed with terminal olefins to produce polyalkenes which are interpolymers. For this invention, a particular polymerized olefin monomer which can be classified as both a terminal olefin and an internal olefin, will be deemed a terminal olefin. Thus, pentadiene-1,3 (i.e., piperylene) is deemed to be a terminal olefin.

While the polyalkenes generally are hydrocarbon polyalkenes, they can contain substituted hydrocarbon groups such as lower alkoxy, lower alkyl mercapto, hydroxy, mercapto, and carbonyl, provided the non-hydrocarbon moieties do not substantially interfere with the functionalization or derivatization reactions of this invention. When present, such substituted hydrocarbon groups normally will not contribute more than about 10% by weight of the total weight of the polyalkenes. Since the polyalkene can contain such non-hydrocarbon substituent, it is apparent that the olefin monomers from which the polyalkenes are made can also contain such substituents. As used herein, the term "lower" when used with a chemical group such as in "lower alkyl" or "lower alkoxy" is intended to describe groups having up to seven carbon atoms.

The polyalkenes may include aromatic groups and cycloaliphatic groups such as would be obtained from polymerizable cyclic olefins or cycloaliphatic substituted-polymerizable acrylic olefins. There is a general preference for polyalkenes free from aromatic and cycloaliphatic groups (other than the diene styrene interpolymer exception already noted). There is a further preference for polyalkenes derived from homopolymers and interpolymers of terminal hydrocarbon olefins of 2 to 16 carbon atoms. This further preference is qualified by the proviso that, while interpolymers of terminal olefins are usually preferred, interpolymers optionally containing up to about 40% of polymer units derived from internal olefins of up to about 16 carbon atoms are also within a preferred group. A more preferred class of polyalkenes are those selected from the group consisting of homopolymers and interpolymers of terminal olefins of 2 to 6 carbon atoms, more preferably 2 to 4 carbon atoms. However, another preferred class of polyalkenes are the latter, more preferred polyalkenes optionally containing up to about 25% of polymer units derived from internal olefins of up to about 6 carbon atoms.

Specific examples of terminal and internal olefin monomers which can be used in the process and to prepare the polyalkenes according to conventional, well-known polymerization techniques include ethylene; propylene; butene-1; butene-2; isobutene; pentene-1; etc; propylene-tetramer; diisobutylene; isobutylene timer; butadiene-1,2; butadiene-1,3; pentadiene-1,2; pentadiene-1,3; etc., $C_6$ to $C_{12}$ olefins, $C_{13}$ to $C_{24}$, and $C_{24}$ to $C_{29}$ middle olefins.

Useful polymers include alpha-olefin homopolymers and interpolymers, and ethylene alpha-olefin copolymers and terpolymers. Specific examples of polyalkenes include polypropylenes, polybutenes, ethylene-propylene copolymers, ethylene-butene copolymers, propylene-butene copolymers, styrene-isobutene copolymers, isobutene-butadiene-1,3 copolymers, etc., and terpolymers of isobutene, styrene and piperylene and copolymer of 80% of ethylene and 20% of propylene. A useful source of polyalkenes are the poly(isobutene)s obtained by polymerization of $C_4$ refinery stream having a butene content of about 35 to about 75% by wt., and an isobutene content of about 30 to about 60% by wt., in the presence of a Lewis acid catalyst such as aluminum trichloride or boron trifluoride. Also useful are the high molecular weight poly-n-butenes of U.S. Ser. No. 992,871 filed Dec. 17, 1992. A preferred source of monomer for making poly-n-butenes is petroleum feedstreams such as Raffinate II. These feedstocks are disclosed in the art such as in U.S. Pat. No. 4,952,739.

Preferred polymers are polymers of ethylene and at least one alpha-olefin having the formula $H_2C=CHR^4$ wherein $R^4$ is straight chain or branched chain alkyl radical comprising 1 to 18 carbon atoms and wherein the polymer contains a high degree of terminal ethenylidene unsaturation. Preferably $R^4$ in the above formula is alkyl of from 1 to 8 carbon atoms and more preferably is alkyl of from 1 to 2 carbon atoms. Therefore, useful comonomers with ethylene in this invention include propylene, 1-butene, hexene-1, octene-1, etc., and mixtures thereof (e.g. mixtures of propylene and 1-butene, and the like). Preferred polymers are copolymers of ethylene and propylene and ethylene and butene-1.

The molar ethylene content of the polymers employed is preferably in the range of between about 20 and about 80%, and more preferably between about 30 and about 70%. When butene-1 is employed as comonomer with ethylene, the ethylene content of such copolymer is most preferably between about 20 and about 45 wt. %, although higher or lower ethylene contents may be present. The most preferred ethylene-butene-1 copolymers are disclosed in U.S. Ser. No. 992,192, filed Dec. 17, 1992. The preferred method for making low molecular weight ethylene/α-olefin copolymer is described in U.S. Ser. No. 992,690, filed Dec. 17, 1992.

Preferred ranges of number average molecular weights of polymer for use as precursors for dispersants are from 500 to 10,000, preferably from 1,000 to 8,000, most preferably from 2,500 to 6,000. A convenient method for such determination is by size exclusion chromatography (also known as gel permeation chromatography (GPC)) which additionally provides molecular weight distribution information. Such polymers generally possess an intrinsic viscosity (as measured in tetralin at 135° C.) of between 0.025 and 0.6 dl/g, preferably between 0.05 and 0.5 dl/g, most preferably between 0.075 and 0.4 dl/g. These polymers preferably exhibit a degree of crystallinity such that, when grafted, they are essentially amorphous.

The preferred ethylene alpha-olefin polymers are further characterized in that up to about 95% and more of the polymer chains possess terminal vinylidene-type unsaturation. Thus, one end of such polymers will be of the formula POLY-C($R^{11}$)=$CH_2$ wherein $R^{11}$ is $C_1$ to $C_{18}$ alkyl, preferably $C_1$ to $C_8$ alkyl, and more preferably methyl or ethyl and wherein POLY represents the polymer chain. A minor amount of the polymer chains can contain terminal ethenyl unsaturation, i.e. POLY-CH=$CH_2$, and a portion of the polymers can contain internal monounsaturation, e.g. POLY-CH=CH($R^{11}$), wherein $R^{11}$ is as defined above.

The preferred ethylene alpha-olefin polymer comprises polymer chains, at least about 30% of which possess terminal vinylidene unsaturation. Preferably at least about 50%, more preferably at least about 60%, and most preferably at least about 75% (e.g. 75 to 98%), of such polymer chains exhibit terminal vinylidene unsaturation. The percentage of polymer chains exhibiting terminal vinylidene unsaturation may be determined by FTIR spectroscopic analysis, titration, HNMR, or $C_{13}$NMR.

The polymers can be prepared by polymerizing monomer mixtures comprising ethylene with other monomers such as alpha-olefins, preferably from 3 to 4 carbon atoms in the presence of a metallocene catalyst system comprising at least one metallocene (e.g., a cyclopentadienyl-transition metal compound) and an activator, e.g. alumoxane compound. The comonomer content can be controlled through selection of the metallocene catalyst component and by controlling partial pressure of the monomers.

The polymer for use in the present invention can include block and tapered copolymers derived from monomers comprising at least one conjugated diene with at least monovinyl aromatic monomer, preferably styrene. Such polymers should not be completely hydrogenated so that the polymeric composition contains olefinic double bonds, preferably at least one bond per molecule. The present invention can also include star polymers as disclosed in patents such as U.S. Pat. Nos. 5,070,131; 4,108,945; 3,711,406; and 5,049,294.

The letter n of formula (I) is greater than 0 and represents the functionality (F) or average number of functional groups per polymer chain. Thus, functionality can be expressed as the average number of moles of functional groups per "mole of polymer". It is to be understood that the term "mole of polymer" includes both functionalized and unfunctionalized polymer, so that F which corresponds to n of Formula (I). The functionalised polymer will include molecules having no functional groups. Specific preferred embodiments of n include $1 \geq n > 0$; $2 \geq n > 1$; and n>2. n can be determined by $C^{13}$ NMR. The optimum number of functional groups needed for desired performance will typically increase with number average molecular weight of the polymer. The maximum value of n will be determined by the number of double bonds per polymer chain in the unfunctionalized polymer.

In specific and preferred embodiments the "leaving group" (-$YR^3$) has a pKa of less than or equal to 12, preferably less than 10, and more preferably less than 8. The pKa is determined from the corresponding acidic species HY-$R^3$ in water at room temperature. Where the leaving group is a simple acid or alkyl ester, the functionalized polymer is very stable especially as the % neo substitution increases. The present invention is especially useful to make "neo" functionalized polymers which are generally more stable and less labile than iso structures. In preferred embodiments the polymer can be at least 60, more preferably at least 80 mole % neofunctionalized. The polymer can be greater than 90, or 99 and even about 100 mole % neo. In one preferred composition the polymer defined by formula (I), Y is O (oxygen), $R^1$ and $R^2$ can be the same or different and are selected from H, a hydrocarbyl group, and a polymeric group.

In another preferred embodiment Y is O or S, $R^1$ and $R^2$ can be the same or different and are selected from H, a hydrocarbyl group a substituted hydrocarbyl group and a polymeric group, and $R^3$ is selected from a substituted hydrocarbyl group, an aromatic group and a substituted aromatic group. This embodiment is generally more reactive towards derivatization with amines and alcohol compounds especially where the $R^3$ substituent contains electron withdrawing species. It has been found that in this embodiment, a preferred leaving group, HY$R^3$, has a pKa of less than 12, preferably less than 10 and more preferably 8 or less. pKa values can range typically from 5 to 12, preferably from 6 to 10, and most preferably from 6 to 8. The pKa of the leaving group determines how readily the system will react with derivatizing compounds to produce derivatized product.

In a particularly preferred composition, $R^3$ is represented by the formula:

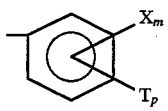

wherein X, which may be the same or different, is an electron withdrawing substituent, T, which may be the same or different, represents a non-electron withdrawing substituent (e.g. electron donating), and m and p are from 0 to 5 with the sum of m and p being from 0 to 5. More preferably, m is from 1 to 5 and preferably 1 to 3. In a particularly preferred embodiment X is selected from a halogen, preferably F or Cl, $CF_3$, cyano groups and nitro groups and p=0. A preferred $R^3$ is derived from 2,4-dichlorophenol.

The composition of the present invention includes derivatized polymer which is the reaction product of the Koch functionalized polymer and a derivatizing compound. Preferred derivatizing compounds include nucleophilic reactant compounds including amines, alcohols, amino-alcohols, metal reactant compounds and mixtures thereof. Derivatized polymer will typically contain at least one of the following groups: amide, imide, oxazoline, and ester, and metal salt. The suitability for a particular end use may be improved by appropriate selection of the polymer Mn and functionality used in the derivatized polymer as discussed hereinafter.

The Koch reaction permits controlled functionalization of unsaturated polymers. When a carbon of the carbon-carbon double bond is substituted with hydrogen, it will result in an "iso" functional group, i.e. one of $R^1$ or $R^2$ of Formula I is H; or when a carbon of the double bond is fully substituted with hydrocarbyl groups it will result in an "neo" functional group, i.e. both $R^1$ or $R^2$ of Formula I are non-hydrogen groups. Polymers produced by processes which result in a terminally unsaturated polymer chain can be functionalized to a relatively high yield in accordance with the process of the present invention. It has been found that the neo acid functionalized polymer can be derivatized to a relatively high yield. The Koch process also makes use of relatively inexpensive materials i.e., carbon monoxide at relatively low temperatures and pressures. Also the leaving group $-YR^3$ can be removed and recycled upon derivatizing the Koch functionalized polymer with amines or alcohols.

The functionalized or derivatized polymers of the present invention are useful as lubricant additives such as dispersants, viscosity improvers and multifunctional viscosity improvers.

The present invention includes oleaginous compositions comprising the above functionalized, and/or derivatized polymer. Such compositions include lubricating oil compositions and concentrates.

The invention also provides a process which comprises the step of catalytically reacting in admixture:

(a) at least one hydrocarbon (polymer) having a number average molecular weight of at least about 500, and an average of at least one ethylenic double bond per polymer chain;

(b) carbon monoxide, (c) at least one acid catalyst, and (d) a nucleophilic trapping agent selected from the group consisting of water, hydroxy-containing compounds and thiol-containing compounds, the reaction being conducted a) in the absence of reliance on transition metal as a catalyst; or b) with at least one acid catalyst having a Hammett acidity of less than −7; or c) wherein functional groups are formed at least 40 mole % of the ethylenic double bonds; or d) wherein the nucleophilic trapping agent has a pKa of less than 12.

The process of the present invention relates to an olefin/polymer having at least one ethylenic double bond reacted via a Koch mechanism to form carbonyl or thio carbonyl group-containing compounds, which may subsequently be derivatized. The polymers react with carbon monoxide in the presence of an acid catalyst or a catalyst preferably complexed with the nucleophilic trapping agent. A preferred catalyst is $BF_3$ and preferred catalyst complexes include $BF_3 \cdot H_2O$ and $BF_3$ complexed with 2,4-dichlorophenol. The starting polymer reacts with carbon monoxide at points of unsaturation to form either iso- or neo-acyl groups with the nucleophilic trapping agent, e.g. with water, alcohol (preferably a substituted phenol) or thiol to form respectively a carboxylic acid, carboxylic ester group, or thio ester.

In a preferred process, at least one polymer having at least one carbon-carbon double bond is contacted with an acid catalyst or catalyst complex having a Hammett Scale acidity value of less than −7, preferably from −8.0 to −11.5 and most preferably from −10 to −11.5. Without wishing to be bound by any particular theory, it is believed that a carbenium ion may form at the site of one of carbon-carbon double bonds. The carbenium ion may then react with carbon monoxide to form an acylium cation. The acylium cation may react with at least one nucleophilic trapping agent as defined herein.

The continuous process of the present invention is especially advantageous with viscous polymer olefins. The tubular or pipe reactor does not rely on turbulent flow to provide mixing but operates in the laminar flow regime. In a preferred embodiment, an ethylene/butene copolymer olefin is reacted with gaseous functionalizing agent, conveniently carbon monoxide and an alcohol such as 2,4-dichlorophenol or other suitable hydroxylic trapping agent in the presence of catalyst, conveniently $BF_3$ to produce ester product in high yield from a reduced (compared to batch operations) reactor volume. Reduced inventories of hazardous materials for equivalent throughput, automated operation with recycle of vapor phase reactant, and more tightly sealed conditions reduce the chance of accidental release. Alkylation side reactions are greatly reduced by the continuous process of the present invention; at high CO partial pressures, reaction conditions and residence times can be controlled to minimize alkylation of the phenol and other side reactions. For some embodiments of the invention, e.g. CSTR, higher portions of some components lower viscosity, which in turn promotes more rapid dissolution of CO gas in the mixture, thereby decreasing alkylation. Thus, higher nucleophilic trapping agent to polymer ratios minimize alkylation.

At least 40 mole %, preferably at least 50 mole %, more preferably at least 80 mole %, and most preferably 90 mole % of the olefin/polymer double bonds will react to form acyl groups wherein the non-carboxyl portion of the acyl group is determined by the identity of the nucleophilic trapping agent, i.e. water forms acid, alcohol forms acid ester and thiol forms thio ester. The polymer functionalized by the recited process of the present invention can be isolated using fluoride salts. The fluoride salt can be selected from the group consisting of ammonium fluoride, and sodium fluoride.

Preferred nucleophilic trapping agents are selected from the group consisting of water, monohydric alcohols, polyhydric alcohols hydroxyl-containing aromatic compounds and hetero substituted phenolic compounds. The catalyst and nucleophilic trapping agent can be added separately or combined to form a catalytic complex. Following is an example of a terminally unsaturated polymer reacted via the Koch mechanism to form an acid or an ester. The polymer is contacted with carbon monoxide or a suitable carbon monoxide source such as formic acid in the presence of an acidic catalyst. The catalyst contributes a proton to the carbon-carbon double bond to form a carbenium ion. This is followed by addition of CO to form an acylium ion which reacts with the nucleophilic trapping agent. POLY, Y, $R^1$, $R^2$ and $R^3$ are defined as above.

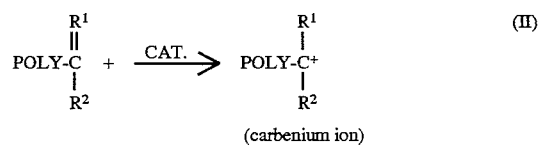

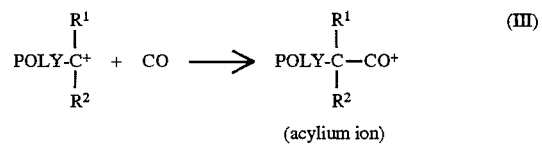

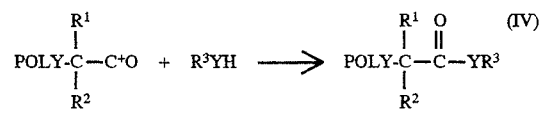

The Koch reaction is particularly useful to functionalize poly(alpha olefins) and ethylene alpha olefin copolymers formed using metallocene-type catalysts. These polymers contain terminal vinylidene groups. There is a tendency for such terminal groups to predominate and result in neo-type (tertiary) carbenium ions. In order for the carbenium ion to form, the acid catalyst is preferably relatively strong. However, the strength of the acid catalyst is preferably balanced against detrimental side reactions which can occur when the acid is too strong. The Koch catalyst can be employed by preforming a catalyst complex with the proposed nucleophilic trapping agent or by adding the catalyst and trapping agent separately to the reaction mixture. This later embodiment has been found to be a particular advantage since it eliminates the step of making the catalyst complex. The following are examples of acidic catalyst and catalyst complex materials with their respective Hammett Scale Value acidity: 60% $H_2SO_4$, −4.32; $BF_3.3H_2O$, −4.5; $BF_3.2H_2O$, −7.0; $WO_3/Al_2O_3$, less than −8.2; $SiO_2/Al_2O_3$, less than −8.2; HF, −10.2; $BF_3.H_2O$, −11.4 to −11.94; $ZrO_2$ less than −12.7; $SiO_2/Al_2O_3$, −12.7 to −13.6; $AlCl_3$, −13.16 to −13.75; $AlCl_3/CuSO_4$, −13.75 to −14.52.

It has been found that $BF_3.2H_2O$ is ineffective at functionalizing polymer through a Koch mechanism ion with polymers. In contrast, $BF_3.H_2O$ resulted in high yields of carboxylic acid for the same reaction. The use of $H_2SO_4$ as a catalyst involves control of the acid concentration to achieve the desired Hammett Scale Value range. Preferred catalysts are $H_2SO_4$ and $BF_3$ catalyst systems. Suitable $BF_3$ catalyst complexes for use in the present invention can be represented by the formula:

$$BF_3.xHOR$$

wherein R can represent hydrogen, hydrocarbyl (as defined below in connection with R')—CO—R', —$SO_2$—R', —PO—$(OH)_2$, and mixtures thereof wherein R' is hydrocarbyl, typically alkyl, e.g., $C_1$ to $C_{20}$ alkyl, and, e.g., $C_6$ to $C_{14}$ aryl, aralkyl, and alkaryl, and x is less than 2.

Following reaction with CO, the reaction mixture is further reacted with water or another nucleophilic trapping agent such as an alcohol or phenolic, or thiol compound. The use of water releases the catalyst to form an acid. The use of hydroxy trapping agents releases the catalyst to form an ester, the use of a thiol releases the catalyst to form a thio ester.

Koch product, also referred to herein as functionalized polymer, typically will be derivatized as described hereinafter. Derivatization reactions involving ester functionalized polymer will typically have to displace the alcohol derived moiety therefrom. Consequently, the alcohol derived portion of the Koch functionalized polymer is sometimes referred to herein as a leaving group. The ease with which a leaving group is displaced during derivatization will depend on its acidity, i.e. the higher the acidity the more easily it will be displaced. The acidity in turn of the alcohol is expressed in terms of its pKa.

Preferred nucleophilic trapping agents include water and hydroxy group containing compounds. Useful hydroxy trapping agents include aliphatic compounds such as monohydric and polyhydric alcohols or aromatic compounds such as phenols and naphthols. The aromatic hydroxy compounds from which the esters of this invention may be derived are illustrated by the following specific example: phenol, -naphthol, cresol, resorcinol, catechol, 2-chlorophenol. Particularly preferred is 2,4-dichlorophenol.

The alcohols preferably can contain up to about 40 aliphatic carbon atoms. They may be monohydric alcohols such as methanols, ethanol, benzyl alcohol, 2-methylcyclohexanol, beta-chloroethanol, monomethyl ether of ethylene glycol, etc. The polyhydric alcohols preferably contain from 2 to about 5 hydroxy radicals; e.g., ethylene glycol, diethylene glycol. Other useful polyhydric alcohols include glycerol, monomethyl ether of glycerol, and pentaerythritol. Useful unsaturated alcohols include allyl alcohol, and propargyl alcohol.

Particularly preferred alcohols include those having the formula $R*_2CHOH$ where an $R*$ is independently hydrogen, an alkyl, aryl, hydroxyalkyl, or cycloalkyl. Specific alcohols include alkanols such as methanol, ethanol, etc. Also preferred useful alcohols include aromatic alcohols, phenolic compounds and polyhydric alcohols as well as monohydric alcohols such as 1,4-butanediol. It has been found that neo-acid ester functionalized polymer is extremely stable due, it is believed, to steric hindrance. Consequently, the yield of derivatized polymer obtainable therefrom will vary depending on the ease with which a derivatizing compound can displace the leaving group of the functionalized polymer.

The most preferred alcohol trapping agents may be obtained by substituting a phenol with at least one electron withdrawing substituent such that the substituted phenol possesses a pKa within the above described preferred pKa ranges. In addition, phenol may also be substituted with at least one non-electron withdrawing substituent (e.g., electron donating), preferably at positions meta to the electron withdrawing substituent to block undesired alkylation of the phenol by the polymer during the Koch reaction. This further improves yield to desired ester functionalized polymer. Accordingly, and in view of the above, the most preferred trapping agents are phenolic and substituted phenolic compounds represented by the formula:

(V)

wherein X, which may be the same or different, is an electron withdrawing substituent, and T which may be the same or different is a non-electron withdrawing group; m and p are from 0 to 5 with the sum of m and p being from 0 to 5, and m is preferably from 1 to 5, and more preferably, m is 1 or 2. X is preferably a group selected from halogen, cyano, and nitro, preferably located at the 2- and/or 4-position, and T is a group selected from hydrocarbyl, and hydroxy groups and p is 1 or 2 with T preferably being located at the 4 and/or 6 position. More preferably X is selected from Cl, F, Br, cyano or nitro groups and m is preferably from 1 to 5, more preferably from 1 to 3, yet more preferably 1 to 2, and most preferably 2 located at the 2 and 4 locations relative to —OH.

The relative amounts of reactants and catalyst, and the conditions controlled in a manner sufficient to functionalize typically at least about 40, preferably at least about 80, more preferably at least about 90 and most preferably at least about 95 mole % of the carbon-carbon double bonds initially present in the unfunctionalized polymer.

The amount of $H_2O$, alcohol, or thiol used is preferably at least the stoichiometric amount required to react with the acylium cations. It is preferred to use an excess of alcohol over the stoichiometric amount. The alcohol performs the dual role of reactant and diluent for the reaction. However, the amount of the alcohol or water used should be sufficient to provide the desired yield yet at the same time not dilute the acid catalyst so as to adversely affect the Hammett Scale Value acidity.

The polymer added to the reactant system can be in a liquid phase. Optionally, the polymer can be dissolved in an inert solvent. The yield can be determined upon completion of the reaction by separating polymer molecules which contain acyl groups which are polar and hence can easily be separated from unreacted non-polar compounds. Separation can be performed using absorption techniques which are known in the art. The amount of initial carbon-carbon double bonds and carbon-carbon double bonds remaining after the reaction can be determined by $C^{13}$ NMR techniques.

In accordance with the process, the polymer is heated to a desired temperature range which is typically between −20° C. to 200° C., preferably from 0° C. to 80° C. and more preferably from 40° C. to 65° C. Temperature can be controlled by heating and cooling means applied to the reactor. Since the reaction is exothermic usually cooling means are required. Mixing is conducted throughout the reaction to assure a uniform reaction medium. For the continuous process of the invention, a suitable temperature operating range is 0°–100° C., conveniently 40°–80° C., preferably 55°–100° C. For more viscous reaction mixtures, temperatures of at least about 80° C. are effective.

The catalyst (and nucleophilic trapping agent) can be prereacted to form a catalyst complex or are charged separately in one step to the reactor to form the catalyst complex in situ at a desired temperature and pressure, preferably under nitrogen. In a preferred system the nucleophilic trapping agent is a substituted phenol used in combination with $BF_3$. The reactor contents are continuously mixed and then rapidly brought to a desired operating pressure using a high pressure carbon monoxide source. Useful pressures can be up to 138,000 kPa (20,000 psig), and typically will be at least 2,070 kPa (300 psig), preferably at least 5,520 kPa (800 psig), and most preferably at least 6,900 kPa (1,000 psig), and typically will range from 3,450 to 34,500 kPa (500 to 5,000 psig) preferably from 4,485 to 20,700 kPa (650 to 3,000 psig) and most preferably from 4,485 to 13,800 kPa (650 to 2000 psig). The carbon monoxide pressure may be reduced by adding a catalyst such as a copper compound. The catalyst to polymer volume ratio can range from 0.25 to 4, preferably 0.5 to 2 and most preferably 0.75 to 1.3. For the continuous process of the invention, this ratio may be 0.05 to 4.0, conveniently 0.10 to 2, especially 0.20 to 1.5.

Preferably, the polymer, catalyst, nucleophilic trapping agent and CO are fed to the reactor in a single step. The reactor contents are then held for a desired amount of time under the pressure of the carbon monoxide. The reaction time can range up to 5 hrs. and typically 0.5 to 4 and more typically from 1 to 2 hrs. The reactor contents can then be discharged and the product which is a Koch functionalized polymer comprising either a carboxylic acid or carboxylic ester or thiol ester functional groups separated. Upon discharge, any unreacted CO can be vented off. Nitrogen can be used to flush the reactor and the vessel to receive the polymer.

In the preferred continuous process of the present invention, reactants are fed to the process by pumps or compressors and mixed together just before or just after entering the reactor, CSTR or tubular (pipe). Vapor phase reagents such as $BF_3$ and carbon monoxide dissolve into the liquids as the reaction proceeds. A flash is performed at the reactor exit to allow most of the $BF_3$ catalyst and unconsumed CO to be released from the liquid phase and recycled. Second stage separations may be used to remove and recycle excess nucleophilic trapping agent/hydroxylic trapping agent such as alcohols, e.g. 2,4-dichlorophenol.

In the CSTR type reactor configuration, liquid and vapor phase reactants are fed to the single stage reactor equipped with mechanical agitator to promote liquid/gas contact and provide uniform concentrations throughout the reactor. The CSTR configuration of the invention may use more than one reactor vessel/stage in series although a single stage is simpler and less expensive. Multiple stages may be used to reduce total volume and residence time. In the tubular reactor, in-line mixers are spaced at intervals to promote liquid/vapor contact in a minimal total volume configuration with no mechanical seals. The in-line mixers may be either static or mechanical (including those with external driven impellers). The mixers are effectively positioned at residence time intervals ranging from 0.25 to 5 min., conveniently 0.25 to 3 min., especially 0.5 to 1.5 min. between mixers. The internal between mixers increases from the inlet to the exit of the reactor.

Each mixer provides homogeneous blending of the liquid and disperses gas bubbles ranging in size from 0.01 to 3 mm, conveniently 0.1 to 2 mm, especially 0.1 to 1 mm. Mixer intensity may be relaxed toward the reactor exit as high gas/liquid contacting is primarily required in the front part of the reactor (although homogeneous blending is needed at the exit). Therefore, gas dispersing mixers are preferred in the front of the tubular reactor and blending mixers are preferred in the back end of the reactor. The Sulzer SMV static mixer is a suitable mixer for gas/liquid contact. Mixers can be designed to optimize bubble size and distribution in a reactor. Larger equipment requires larger mixers. Each mixer has a series of elements as splitting/remixing devices, typically four, which split and remix the flow several times. The preferred continuous process of the invention includes a laminar flow process where the Reynolds Number is very low, preferably less than 10, and uses static mixers to disperse gas into liquid and promote reaction. The mixers are followed by open pipe to provide residence time for reaction.

The tubular reactor process is also advantageous because it eliminates the need for liquid level control, has simple controls and operation, has a short reaction time, provides high yields, maximizes inherent safety; and permits use of a wide range of polymer viscosity. The continuous process of the invention also provides a very clean, white product compared to batch preparations, especially where exposure to air and oxygen are avoided.

Depending on the particular reactants employed, the functionalized polymer containing reaction mixture may be a single phase, a combination of a partitionable polymer and acid phase or an emulsion with either the polymer phase or acid phase being the continuous phase. Upon completion of the reaction, the polymer is recovered by suitable means. In some cases it may be necessary to quickly separate or neutralize catalyst components upon recovery of product to avoid reversion of desired ester product to starting material or other by-product (e.g., rapidly lower pressure and increase temperature to promote $BF_3$ release; or quench with excess leaving group or neutralizing agent). When the mixture is an emulsion, a suitable means can be used to separate the polymer. A preferred means is the use of fluoride salts, such as sodium or ammonium fluoride in combination with an alcohol such as butanol or methanol to neutralize the catalyst and phase separate the reaction complex. The fluoride ion helps trap the $BF_3$ complexed to the functionalized polymer and helps break emulsions generated when the crude product is washed with water. Alcohols such as methanol and butanol and commercial demulsifiers also help to break emulsions especially in combination with fluoride ions. Preferably, nucleophilic trapping agent is combined with the fluoride salt and alcohols when used to separate polymers. The presence of the nucleophilic trapping agent as a solvent minimizes transesterification of the functionalized polymer.

Where the nucleophilic trapping agent has a pKa of less than 12 the functionalized polymer can be separated from the nucleophilic trapping agent and catalyst by depressurization and distillation. It has been found that where the nucleophilic trapping agent has lower pKa's, the catalyst, i.e. $BF_3$ releases more easily from the reaction mixture.

As indicated above, polymer which has undergone the Koch reaction is also referred to herein as functionalized polymer. Thus, a functionalized polymer comprises molecules which have been chemically modified by at least one functional group so that the functionalised polymer is (a) capable of undergoing further chemical reaction (e.g. derivatization) or (b) has desirable properties, not otherwise possessed by the polymer alone, absent such chemical modification.

It will be observed from the discussion of formula I that the functional group is characterized as being represented by the parenthetical expression

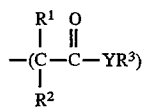

which expression contains the acyl group

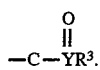

It will be understood that while

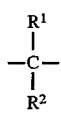

moiety is not added to the polymer in the sense of being derived from a separate reactant it is still referred to as being part of the functional group for ease of discussion and description. Strictly speaking, it is the acyl group which constitutes the functional group, since it is this group which is added during chemical modification. Moreover, $R^1$ and $R^2$ represent groups originally present on, or constituting part of, the 2 carbons bridging the double bond before functionalization. However, $R_1$ and $R_2$ were included within the parenthetical so that neo acyl groups could be differentiated from iso acyl groups in the formula depending on the identity of $R_1$ and $R_2$.

Typically, where the end use of the polymer is for making dispersant, e.g. as derivatized polymer, the polymer will possess dispersant range molecular weights (Mn) as defined hereinafter and the functionality will typically be significantly lower than for polymer intended for making derivatized multifunctional V.I. improvers, where the polymer will possess viscosity modifier range molecular weights (Mn) as defined hereinafter.

Accordingly, while any effective functionality can be imparted to functionalized polymer intended for subsequent derivatization, it is contemplated that such functionalities, expressed as F, for dispersant end uses, are typically not greater than about 3, preferably not greater than about 2, and typically can range from about 0.5 to about 3, preferably from 0.8 to about 2.0 (e.g. 0.8 to 1). Similarly, effective functionalities F for viscosity modifier end uses of derivatized polymer are contemplated to be typically greater than about 3, preferably greater than about 5, and typically will range from 5 to about 10. End uses involving very high molecular weight polymers contemplate functionalities which can range typically greater than about 20, preferably greater than about 30, and most preferably greater than about 40, and typically can range from 20 to 60, preferably from 25 to 55 and most preferably from 30 to 50.

Referring now to FIG. 1, a jacketed pipe reactor and associated equipment, suitable for demonstration, are shown. Polymer and nucleophilic trapping agent such as 2,4-dichlorophenol are mixed in feed tank 2 and fed continuously by pump 4 to reactor 6. CO and catalyst, conveniently $BF_3$ gas, are provided as make-up through mass flow controllers 8 and 10 to recycle gas line 12, compressor 14, and mass flow controller 16 to main feed line 18. The reactor 6 has a series of tubes 20 having insulating jackets 22. The first eight tubes have two static mixers 24 positioned as shown and the second eight tubes have only one static mixer 24 per tube as shown. The reactor 6 may be reversed from the position shown to provide a different mixing profile but still operating in laminar flow with entrained gas.

The reaction mass flows through flash drums 26 and 28 to provide recycle gases to line 12 and the nucleophilic trapping agent, conveniently 2,4-dichlorophenol, is collected at 30 by use of vacuum and heat. The product is moved by pump 32, preferably through a wiped film evaporator 34 to separate light ends at 36 and collect product, preferably ester, in drum 38. This description may not be suitable for all operations. Nucleophilic trapping agent, such as 2,4-dichlorophenol, and polymer/olefin may be fed separately and could be blended after gas introduction. Jackets may be varied to maintain a desired temperature profile. Temperature may also be controlled by: precooling feeds and allowing the heat of reaction to bring temperature up; preheating feed, e.g. 100° C., and using cooling jackets. Preferably, the temperature is maintained in the preferred range throughout the reactor and the desired temperature is achieved within the first half, preferably the first quarter of the reactor length. Enhanced heat transfer devices may be used, such as jacketed tubes containing static mixer elements to increase heat transfer coefficient (with reaction mass mixing) or tubes with internal cooling coils to provide more surface area and heat transfer coefficient (e.g., Sulzer SMR mixer/exchangers).

U.S. Ser. No. 261,507, Amidation of Ester Functionalized Polymers; U.S. Ser. No. 261,557, Prestripped Polymer Used to Improve Koch Reaction Dispersant Additives; U.S. Ser. No. 261,559, Batch Koch Carbonylation Process; U.S. Ser. No. 261,534, Derivatives of Polyamines With One Primary Amine and Secondary or Tertiary Amines; U.S. Ser. No. 261,554, Lubricating Oil Dispersants Derived from Heavy Polyamines; and U.S. Ser. No. 261,558, Functionalized Additives Useful In Two-Cycle Engines, all filed Jun. 17, 1994, all contain related subject matter as indicated by their titles and are hereby incorporated by reference in their entirety for all purposes.

Derivatized Polymers

The functionalized polymer can be used as a dispersant/multifunctional viscosity modifier if the functional group contains the requisite polar group. The functional group can also enable the polymer to participate in a variety of chemical reactions. Derivatives of functionalized polymers can be formed through reaction of the functional group. These derivatized polymers may have the requisite properties for a variety of uses including use as dispersants and viscosity modifiers. A derivatized polymer is one which has been chemically modified to perform one or more functions in a significantly improved way relative to the unfunctionalized polymer and/or the functionalized polymer. Representative of such functions, are dispersancy and/or viscosity modification in lubricating oil compositions.

The derivatizing compound typically contains at least one reactive derivatizing group selected to react with the functional groups of the functionalized polymers by various reactions. Representative of such reactions are nucleophilic substitution, transesterification, salt formation, and the like. The derivatizing compound preferably also contains at least one additional group suitable for imparting the desired properties to the derivatized polymer, e.g., polar groups. Thus, such derivatizing compounds typically will contain one or more groups including amine, hydroxy, ester, amide, imide, thio, thioamido, oxazoline, or carboxylate groups or form such groups at the completion of the derivatization reaction.

The derivatized polymers include the reaction product of the above recited functionalized polymer with a nucleophilic reactant which include amines, alcohols, amino-alcohols and mixtures thereof to form oil soluble salts, amides, oxazoline, and esters. Alternatively, the functionalized polymer can be reacted with basic metal salts to form metal salts of the polymer. Preferred metals are Ca, Mg, Cu, Zn, Mo, and the like. Suitable properties sought to be imparted to the derivatized polymer include one or more of dispersancy, multifunctional viscosity modification, antioxidancy, friction modification, antiwear, antirust, seal swell, and the like. The preferred properties sought to be imparted to the derivatized polymer include dispersancy (both mono- and multifunctional) and viscosity modification primarily with attendant secondary dispersant properties. A multifunctional dispersant typically will function primarily as a dispersant with attendant secondary viscosity modification.

While the Koch functionalization and derivatization techniques for preparing multifunctional viscosity modifiers (also referred to herein as multifunctional viscosity index improvers or MFVI) are the same as for ashless dispersants, the functionality of a functionalized polymer intended for derivatization and eventual use as an MFVI will be controlled to be higher than functionalized polymer intended for eventual use as a dispersant. This stems from the difference in Mn of the MFVI polymer backbone vs. the Mn of the dispersant polymer backbone. Accordingly, it is contemplated that an MFVI will be derived from functionalized polymer having typically up to about one and at least about 0.5 functional groups, (i.e. "n" of formula (I)) for each 20,000, preferably for each 10,000, most preferably for each 5,000 Mn molecular weight segment in the backbone polymer.

Dispersants maintain oil insolubles, resulting from oil use, in suspension in the fluid thus preventing sludge flocculation and precipitation. Suitable dispersants include, for example, dispersants of the ash-producing (also known as detergents) and ashless type, the latter type being preferred. The derivatized polymer compositions of the present invention, can be used as ashless dispersants and multifunctional viscosity index improvers in lubricant and fuel compositions.

At least one functionalized polymer is mixed with at least one of amine, alcohol, including polyol, aminoalcohol, etc., to form the dispersant additives. One class of particularly preferred dispersants are those derived from the functionalized polymer of the present invention reacted with (i) hydroxy compound, e.g., a polyhydric alcohol or polyhydroxy-substituted aliphatic primary amine such as pentaerythritol or trismethylolaminomethane (ii) polyoxyalkylene polyamine, e.g. polyoxypropylene diamine, and/or (iii) polyalkylene polyamine, e.g., polyethylene polyamine such as tetraethylene pentamine referred to herein as TEPA.

Useful amine compounds for derivatizing functionalized polymers comprise at least one amine and can comprise one or more additional amine or other reactive or polar groups. Where the functional group is a carboxylic acid, carboxylic ester or thiol ester, it reacts with the amine to form an amide. Preferred amines are aliphatic saturated amines. Non-limiting examples of suitable amine compounds include: 1,2-diaminoethane; 1,3-diaminopropane; 1,4-diaminobutane; 1,6-diaminohexane; polyethylene amines such as diethylene triamine; triethylene tetramine; tetraethylene pentamine; etc.

Other useful amine compounds include: alicyclic diamines such as 1,4-di(aminomethyl) cyclohexane, and heterocyclic nitrogen compounds such as imidazolines. Mixtures of amine compounds may advantageously be used. Useful amines also include polyoxyalkylene polyamines. A particularly useful class of amines are the polyamido and related amines.

The functionalized polymers of the present invention can be reacted with alcohols, e.g. to form esters. The alcohols may be aliphatic compounds such as monohydric and polyhydric alcohols or aromatic compounds such as phenols and naphthols. The aromatic hydroxy compounds from which the esters may be derived are illustrated by the following specific examples: phenol, beta-naphthol, alpha-naphthol, cresol, resorcinol, catechol, etc. Phenol and alkylated phenols having up to three alkyl substituents are preferred. The alcohols from which the esters may be derived preferably contain up to about 40 aliphatic carbon atoms. They may be monohydric alcohols such as methanols, ethanol, isooctanol, etc. A useful class of polyhydric alcohols are those having at least three hydroxy radicals, some of which have been esterified with a monocarboxylic acid having from about 8 to about 30 carbon atoms, such as octanoic acid, oleic acid, stearic acid, linoleic acid, dodecanoic acid, or tall oil acid.

The esters may also be derived from unsaturated alcohols such as allyl alcohol, cinnamyl alcohol, propargyl alcohol. Still another class of the alcohols capable of yielding the esters of this invention comprise the ether-alcohols and amino-alcohols including, for example, the oxyalkylene-, oxyarylene-, amino-alkylene-, and amino-arylene- substituted alcohols having one or more oxyalkylene, amino-alkylene or amino-arylene oxyarylene radicals. They are exemplified by Cellosolve, carbitol, phenoxyethanol, etc.

The functionalized polymer of this invention is reacted with the alcohols according to conventional esterification, or transesterification techniques. This normally involves heating the functionalized polymer with the alcohol, optionally in the presence of a normally liquid, substantially inert, organic liquid solvent/diluent and/or in the presence of esterification catalyst.

Useful reactive metals or reactive metal compounds are those which will form metal salts of the functionalized polymer or metal-containing complexes with the functionalized polymer. Metal complexes are typically achieved by reacting the functionalized polymers with amines and/or alcohols as discussed above and also with complex forming reactants either during or subsequent to amination.

Complex-forming metal reactants include the nitrates, nitrites, halides, carboxylates, etc.

The appropriate functionalized polymer of this invention can be reacted with any individual derivatizing compound such as amine, alcohol, reactive metal, reactive metal compound or any combination of two or more of any of these; that is, for example, one or more amines, one or more alcohols, one or more reactive metals or reactive metal compounds, or a mixture of any of these. Substantially inert organic liquid diluents may be used to facilitate mixing, temperature control, and handling of the reaction mixture.

The reaction products produced by reacting functionalized polymer of this invention with derivatizing compounds such as alcohols, nitrogen-containing reactants, metal reactants, and the like will, in fact, be mixtures of various reaction products. The functionalized polymers themselves can be mixtures of materials. While the functionalized polymers themselves possess some dispersant characteristics and can be used as dispersant additives in lubricants and fuels, best results are achieved when at least about 30, preferably, at least about 50, most preferably 100% of the functional groups are derivatized.

Functionalized and/or derivatized polymers may be post-treated. The processes for post-treating derivatized polymer are analogous to the post-treating processes used with respect to conventional dispersants and MFVI's of the prior art. Accordingly, the same reaction conditions, ratio of reactants and the like can be used. Accordingly, derivatized polymer can be post-treated with such reagents as urea, thiourea, carbon disulfide, aldehydes, ketones, carboxylic acids, hydrocarbon-substituted succinic anhydrides, nitriles, epoxides, boron compounds, phosphorus compounds or the like.

The amine derivatized polymers of the present invention as described above can be post-treated, particularly for use as dispersants and viscosity index improvers by contacting said polymers with one or more post-treating reagents such as boron compounds, nitrogen compounds, phosphorus compounds, oxygen compounds, succinic acids and anhydrides (e.g., succinic anhydride, dodecyl succinic anhydride, and $C_1$ to $C_{30}$ hydrocarbyl substituted succinic anhydride), other acids and anhydrides such as maleic and fumaric acids and anhydrides, and esters of the foregoing e.g., methyl maleate. The amine derivatized polymers are preferably treated with boron oxide, boron halides, boron acid esters or boron ester in an amount to provide from 0.1–20.0 atomic proportions of boron per mole of nitrogen composition. Borated derivatized polymer useful as dispersants can contain from 0.05 to 2.0 wt. %, e.g. 0.05 to 0.7 wt. % boron based on the total weight of said borated nitrogen-containing dispersant compound. Treating is readily carried out by adding said boron compound, preferably boric acid usually as a slurry, to said nitrogen compound and heating with stirring at from about 135° C. to 190° C., e.g. 140° C. to 170° C., for from 1 to 5 hrs. The derivatized polymers of the present invention can also be treated with polymerizable lactones (such as epsilon-caprolactone) to form dispersant adducts.

The Koch functionalized polymer, in addition to acting as intermediates for dispersant and MFVI manufacture, can be used as molding release agents, molding agents, metal working lubricants, point thickeners and the like. The primary utility for the products of the invention, from functionalized polymer all the way through post-treated derivatized polymer, is as additives for oleaginous compositions.

The additives of the invention may be used by incorporation into an oleaginous material such as fuels and lubricating oils. Fuels include normally liquid petroleum fuels such as middle distillates boiling from 65° C. to 430° C., including kerosene, diesel fuels, home heating fuel oil, jet fuels, etc. A concentration of the additives in the fuel is in the range of typically from 0.001 to 0.5, and preferably 0.005 to 0.15 wt. %, based on the total weight of the composition, will usually be employed.

The additives of the present invention may be used in lubricating oil compositions which employ a base oil in which the additives are dissolved or dispersed therein. Such base oils may be natural or synthetic. Base oils suitable for use in preparing the lubricating oil compositions of the present invention include those conventionally employed as crankcase lubricating oils for spark-ignited and compression-ignited internal combustion engines, such as automobile and truck engines, marine and railroad diesel engines, and the like. Advantageous results are also achieved by employing the additive mixtures of the present invention in base oils conventionally employed in and/or adapted for use as power transmitting fluids, universal tractor fluids and hydraulic fluids, heavy duty hydraulic fluids, power steering fluids and the like. Gear lubricants, industrial oils, pump oils and other lubricating oil compositions can also benefit from the incorporation therein of the additives of the present invention.

Natural oils include animal oils and vegetable oils (e.g., castor, lard oil) liquid petroleum oils and hydrorefined, solvent-treated or acid-treated mineral lubricating oils of the paraffinic, naphthenic and mixed paraffinic-naphthenic types. Oils of lubricating viscosity derived from coal or shale are also useful base oils.

Synthetic lubricating oils include hydrocarbon oils and halosubstituted hydrocarbon oils such as polymerized and interpolymerized olefins (e.g., polybutylenes, polypropylenes, propylene-isobutylene copolymers, chlorinated polybutylenes, etc. Alkylene oxide polymers and interpolymers and derivatives thereof where the terminal hydroxyl groups have been modified by esterification, etherification, etc., constitute another class of known synthetic lubricating oils. Another suitable class of synthetic lubricating oils comprises the esters of dicarboxylic acids. Esters useful as synthetic oils also include those made from $C_5$ to $C_{12}$ monocarboxylic acids and polyols and polyol ethers such as neopentyl glycol, etc. Silicon-based oils such as the polyalkyl-, polyaryl-, polyalkoxy-, or polyaryloxysiloxane oils and silicate oils comprise another useful class of synthetic lubricants. Unrefined, refined and rerefined oils can be used in the lubricants of the present invention.

The additives of the present invention, particularly those adapted for use as dispersants or viscosity modifiers, can be incorporated into a lubricating oil in any convenient way. Thus, they can be added directly to the oil by dispersing or dissolving the same in the oil. Such blending into the additional lube oil can occur at room temperature or elevated temperatures. Alternatively the additives may be first formed into concentrates, which are in turn blended into the oil. Such dispersant concentrates will typically contain as active ingredient (A.I.), from 10 to 80 wt. %, typically 20 to 60 wt. %, and preferably from 40 to 50 wt. %, additive, (based on the concentrate weight) in base oil. MFVI concentrates typically will contain from 5 to 50 wt. % AI.

The additives of the invention may be mixed with other additives selected to perform at least one desired function. Typical of such additional additives are detergents, viscosity modifiers, wear inhibitors, oxidation inhibitors, corrosion inhibitors, friction modifiers, foam inhibitors, rust inhibitors, demulsifiers, antioxidants, lube oil flow improvers, and seal swell control agents.

Compositions, when containing these additives, typically are blended into the base oil in amounts which are effective to provide their normal attendant function. Representative effective amounts of such additives are illustrated as follows:

| Compositions | (Broad) Wt % | (Preferred) Wt % |
|---|---|---|
| V.I. Improver | 1–12 | 1–4 |
| Corrosion Inhibitor | 0.01–3 | 0.01–1.5 |
| Oxidation Inhibitor | 0.01–5 | 0.01–1.5 |
| Dispersant | 0.1–10 | 0.1–5 |
| Lube Oil Flow Improver | 0.01–2 | 0.01–1.5 |
| Detergents and Rust Inhibitors | 0.01–6 | 0.01–3 |
| Pour Point Depressant | 0.01–1.5 | 0.01–1.5 |
| Anti-Foaming Agents | 0.001–0.1 | 0.001–0.01 |
| Antiwear Agents | 0.001–5 | 0.001–1.5 |
| Seal Swellant | 0.1–8 | 0.1–4 |
| Friction Modifiers | 0.01–3 | 0.01–1.5 |
| Lubricating Base Oil | Balance | Balance |

When other additives are employed, it may be desirable, although not necessary, to prepare additive concentrates or packages comprising concentrated solutions or dispersions of the subject additives of this invention together with one or more of said other additives. Dissolution of the additive concentrate into the lubricating oil may be facilitated by solvents and by mixing accompanied with mild heating, but this is not essential. The final formulations may employ typically 2 to 20 wt. %, e.g. about 10 wt. %, of the additive package with the remainder being base oil. All of said weight percents expressed herein (unless otherwise indicated) are based on active ingredient (A.I.) content of the individual additives, and the total weight of the additive package or formulation, which will include the weight of total oil or diluent.

EXAMPLES

Composition parts and percents are by weight unless otherwise indicated. All molecular weights (Mn) are number average molecular weight.

Continuous Process Example A

A CSTR process was conducted at steady state of 73° C. and 12,420 kPa (1800 psig). Ethylene/butene (EB) copolymer having $M_n$ of 3850 and 25 wt. % ethylene content was fed to the reactor at 35 kg/hr. while 2,4-dichlorophenol was separately fed at 11.8 moles per mole EB copolymer. Mixed CO and $BF_3$ gases were fed through a recycle compressor and make-up supply as needed to maintain 8722 kPa (1264 psig) CO partial pressure and 3698 kPa (536 psig) $BF_3$ partial pressure in the vapor space of the reactor. This process operated at 41% of full liquid level with a residence time of 16.3 minutes to provide 91% active ingredient yield as measured by infrared technique (IR). Varying pressures, reactants, temperature, and flow rates provided similar results with conversions up to 91% active ingredient.

Continuous Process Example B

A continuous process was carried out in a pipe reactor having 16 4.27 meter (14 feet) long 2.032 cm (0.8 inch) inside diameter jacketed tubes connected in series. The first eight tubes have a one-half inch (1.27 cm) Sulzer SMV-DY static mixer with 1/16 inch (1.5 mm) plate spacing at the entry and halfway along the length of each tube. Each mixer has four mixing elements. The second set of eight tubes has a single static mixer at the "entry" end of each tube. The reactor may be operated in reverse direction, if desired, to pass reactants first through the eight tubes with a single mixer.

The polymer of Example A was mixed in a feed tank with 2,4-dichlorophenol in a 1:6 molar ratio and fed to the pipe reactor at 37.5 kg/hr. at reactor temperature of 75° C. Recycle carbon monoxide and $BF_3$ (0.26 mole $BF_3$/mole CO) were fed to the reactor at inlet pressure of 12,420 kPa (1800 psig) total pressure to provide an initial gas/liquid volume that was 60% by volume liquid. Steady state operation provided 88.8% conversion, as estimated by IR, to a very clean; white product ester.

Examples 1–13

Yield of Carboxylic Acid Group (Examples 1–5)

Example 1 (Comparative)

34.5 parts of poly-n-butene polymer (PNB) (Mn=550) dissolved in 36.2 parts of n-heptane ($nC_7$) were charged to an autoclave, mixed and heated to 50° C. 662 parts of $BF_3$ dihydrate ($BF_3.2H_2O$) were then charged followed immediately by CO which brought the total autoclave pressure to 1500 psig. The mixture was stirred for 3 hrs. at temperature and pressure. Pressure was released, and the reaction product was washed with copious amounts of water and butanol to free the polymer phase from the acid phase. The polymer was dried in an oven. The analysis of the finished polymer showed less than 5% conversion to the carboxylic acid group.

Example 2

The procedure described in Example 1 was then followed except, 37.1 parts of PNB (Mn=550) was dissolved in 40.2 parts of $nC_7$, and 690 parts of $BF_3.1.2H_2O$ was substituted for the $BF_3.2H_2O$ and prepared by bubbling $BF_3$ gas into $BF_3.2H_2O$ until sufficient $BF_3$ was absorbed to give the desired composition. The pressure was brought to 2000 psig with CO. Analysis of the final product showed 85% conversion of the polymer to neo-carboxylic acid.

Example 3

The procedure described in Example 1 was followed except that 203.6 parts of ethylene propylene (EP) copolymer (Mn=1800, and about 50 wt. % ethylene) and 159.9 parts of $nC_7$, and 34 parts of $BF_3.1.1$ $H_2O$ were substituted for the charges of reactants. The pressure was brought to 2000 psi with CO. The conversion to neo-carboxylic acid was 56%.

Example 4

The procedure described in Example 1 was followed except 803 parts of ethylene butene (EB) copolymer (Mn=3700 about 45 wt. % ethylene), 568 parts of iso-octane, and 670 parts of $BF_3.1.1$ $H_2O$ were used. The pressure was brought to 2000 psig with CO. The reaction product was discharged into an aqueous solution containing 600 parts of sodium fluoride (NaF), 756 parts of water, 302 parts of hexane, and 50 parts of butanol. The polymer product readily separated from the aqueous phase, was recovered, and dried. Analysis showed 85.1% conversion to neo-carboxylic acid.

Example 5

The procedure described in Example 4 was followed except 543 parts of propylene butylene (PB) copolymer (Mn=2800, and about 30 wt. % propylene) 454 parts of iso-octane, and 659 parts of $BF_3 \cdot 1.1 \; H_2O$ were used. The reaction product was discharged into 600 parts sodium fluoride, 945 parts water, and 302 parts hexane. The analysis of the final product showed 75.4% conversion to neo-carboxylic acid. The results of Examples 1–5 are summarized in Table 1 below:

TABLE 1

| Example | Polymer | Mn | Catalyst Complex | Yield (%) |
| --- | --- | --- | --- | --- |
| Comp. | | | | |
| 1 | PNB | 550 | $BF_3 \cdot 2H_2O$ | 5 |
| 2 | PNB | 550 | $BF_3 \cdot 1.2H_2O$ | 85 |
| 3 | EP | 1800 | $BF_3 \cdot 1.1H_2O$ | 56 |
| 4 | EB | 3700 | $BF_3 \cdot 1.1H_2O$ | 85.1 |
| 5 | PB | 2800 | $BF_3 \cdot 1.1H_2O$ | 75.4 |

Alkyl Ester (Examples 6–12)

Example 6 (Comparative)

The procedure described in Example 1 was followed except, 1119.2 parts of PNB (Mn=550) without solvent, and 350 parts of $BF_3$. dibutanol (prepared by bubbling $BF_3$ gas into n-butanol) were used. The pressure was brought to 2000 psig with CO. The analysis of the final product showed less than 5% conversion to neo-alkyl ester.

Example 7

The procedure described in Example 1 was followed except, 153.3 parts of EP polymer (Mn=900, about 50 wt. % ethylene) and 137.9 parts $nC_7$, and 88 parts of $BF_3$.monobutanol was used in the recipe. The polymer was dried, and the conversion to neo-alkyl ester was 86%.

Example 8

The procedure as described in Example 4 was followed except 143 parts of PNB (Mn=550), without solvent, and 37 parts of $BF_3$.monomethanol (prepared by bubbling $BF_3$ gas into methanol) ($BF_3 \cdot CH_3OH$) was used. The reaction product was discharged into 230 parts of ammonium fluoride and 765 parts methanol. The conversion was 91.3% to the neo-methyl ester.

Aryl Ester

Example 9

The procedure described in Example 1 was followed except 440 parts of PNB (Mn=550), without solvent, and 244 parts of $BF_3$.tetra (4-chlorophenol) was used. The $BF_3$ complex was prepared by bubbling $BF_3$ gas into melted 4-chlorophenol. The autoclave was pressured to 1485 psig with CO, and the reaction was held at 55° C. for 2 hrs. Analysis showed the following results:

Yield to 4 chloro phenyl neo-ester/acid=60% of polymer
 to alkyl phenyl ester=11.7% of polymer
 to alkyl phenol=10.1% of polymer
Total Yield=81.8% polymer converted Example 10

(Catalyst Complex)

A complex of $BF_3$ with 4-chlorophenol was prepared by bubbling $BF_3$ into melted 4-chlorophenol. In order to enhance the uptake of $BF_3$ gas to generate $BF_3 \cdot di(4\text{-}chlorophenol)$ the solution was cooled. After several minutes, the solution solidified. Melting the complex resulted in rapid liberation of $BF_3$.

(Carbonylation)

An autoclave was charged with 391 psig of $BF_3$ gas at 30° C., followed by an additional 118 psig of CO, to a total pressure of about 500 psig. While stirring the autoclave, a mixture of 440 parts PNB (Mn=550) and 108 parts of 3-fluoro-phenol was charged to the reactor, and the pressure was brought to 1500 psig with CO, and the temperature to 50° C. The reaction was held at these conditions for 2 hrs. and the autoclave was then depressurized. The reaction product was stripped to remove $BF_3$ gas and excess substituted phenol. The final product analysis showed 91.5% yield.

Example 11

The procedure of Example 10 was followed, except the autoclave was pressured to 199 psig with $BF_3$ at 50° C., followed by 301 psig of CO, to bring the total pressure to 500 psig and 406 parts of EB copolymer (Mn=4600, 20 wt. % ethylene) and 100.6 parts of 2,4-dichlorophenol (pKa= 7.85) at 50° C. were charged to the autoclave and pressured to 1430 psig with CO. The yield was 84.5%.

Example 12

The procedure in Example 10 was followed except the autoclave was pressured to 254 psig with $BF_3$ at 50° C., followed by 254 psig of CO to bring the total pressure to 508 psig; and, 110 parts EB polymer (Mn=2200, about 50% ethylene) 31 parts of dichlorophenol (pKa=7.85) at 50° C. were charged to the autoclave, and pressurized to 2000 psig with CO. The conversion was 85.4%. The results of Examples 6–9 and 10–12 are summarized in Table 2 below:

TABLE 2

| Example | Polymer | Mn | Catalyst Complex | Yield (%) |
| --- | --- | --- | --- | --- |
| Comp. | | | | |
| 6 | PNB | 550 | $BF_3$.dibutanol | 5 |
| 7 | EB | 900 | $BF_3$.monobutanol | 86 |
| 8 | PNB | 550 | $BF_3$.monomethanol | 91.3 |
| 9 | PNB | 550 | $BF_3$.tetra(4-chlorophenol) | 81.8 |
| 10 | PNB | 550 | *$BF_3$ + 3-fuorophenol | 91.5 |
| 11 | EB | 4600 | *$BF_3$ 2,4-dichlorophenol | 84.5 |
| 12 | EB | 2200 | $BF_3$ + dichlorophenol | 85.4 |

*Catalyst and phenolic compound added separately in one step.

Examples 13–17

Amination Reaction of PNB-neo Carboxylic Acid with PAM

Example 13

200 parts the PNB neocarboxylic acid prepared by a process similar to that of Example 2 and 31.2 parts of poly(ethyleneamine) averaging 5–8 nitrogens per molecule (PAM) were charged into a reactor with stirring. The reactor contents were purged with nitrogen. The reactor was sealed and the pressure was brought to 60 psig with nitrogen. The reactor was heated to 240° C. for five hrs. The contents were then sparged with nitrogen via a dip tube and overhead vent line and cooled at 30° C. The yield of carboxylic acid amide by $^{13}C$-NMR was 45.4%.

Example 14

374 parts of neo acid functionalized EB copolymer of Example 4 dissolved in 700 parts heptane were charged to a reactor vessel. The solution was heated with mixing to 90° C. Then, 70 parts of thionyl chloride was slowly added to the solution, plus an additional 300 parts of heptane. After the reaction to the acid chloride was complete, the solution was heated to 100° C. at atmospheric pressure with $N_2$ sparging followed by high vacuum flashing to remove reaction by-products and heptane. The acid chloride product was cooled. Then, fresh, dry heptane was added to the acid chloride product. The acid chloride product was then heated to 90° C. Then, 10 parts of polyamine (PAM) and 17.8 parts of triethylamine were slowly added to the acid chloride. The reaction mixture was filtered and excess triethylamine was stripped to produce the aminated product as shown by infrared analysis.

Example 15

17.8 parts of the 2,4-dichlorophenyl ester of the EB copolymer of Example 11 were charged to a reaction vessel. The vessel contents were heated to 80° C. with mixing. Then 0.442 parts of polyamine (PAM) was charged to the vessel. The vessel contents were than slowly heated over a period of 8 hrs. from 150° C. to 220° C. while refluxing the liberated dichlorophenol (pKa=7.85). After complete conversion to the amide, the phenol was removed by $N_2$ sparging. The vessel contents were cooled to ambient temperature. Carbon$^{13}$ NMR analysis showed quantitative conversion of ester to amide.

Example 16

The procedure as described in Example 15 was followed, except 20.2 parts of the 2,4-dichlorophenyl ester of Example 12 was used with 0.954 parts of PAM. Carbon$^{13}$ NMR analysis showed quantitative conversion of ester to amide.

Example 17

19.4 parts of the aminated polymer described in Example 16 was mixed with 10.0 parts of base oil and heated to 140° C. in a reaction vessel with mixing. Then 1.407 parts of milled 30% boric acid slurry in base oil was slowly added to the vessel contents. The reactor was sparged with $N_2$ at temperature for 2 hrs., then an additional 6.26 parts of base oil was added to the reaction vessel. The vessel contents were cooled to 120° C., and filtered. Analysis of the product showed a 45% active ingredient level (0.73% N, 0.26% B).

We claim:

1. A process for producing a functionalized polymer comprising continuously (A) reacting a polymeric olefin, a nucleophilic trapping agent of formula $HYR^3$ and gaseous carbon monoxide in the presence of an acid catalyst and in the absence of reliance on transition metal catalyst, whereby said polymeric olefin is functionalized by attachment of —CO—YR3 groups, wherein Y is O or S, and $R^3$ is H, hydrocarbyl, aryl, substituted aryl or substituted hydrocarbyl; and (B) recovering functionalized polymer.

2. The process of claim 1 wherein the trapping agent of formula $HYR^3$ has a pKa<12.

3. The process of claim 1 wherein $R^3$ is hydrocarbyl and the recovered functionalized polymer is an ester.

4. The process of claim 1 characterized by reacting said polymeric olefin in a continuous stirred tank reactor.

5. The process of claim 1 characterized by reacting said polymeric olefin in a pipe reactor operated in laminar flow.

6. The process of claim 5 wherein said pipe reactor includes static mixers.

7. The process of claim 6 operated in laminar flow with a Reynolds number of less than 10.

8. A process for producing a functionalized olefin comprising continuously reacting a liquid-phase olefin with gaseous carbon monoxide and a nucleophilic trapping agent of formula $HYR^3$ in the presence of an acid catalyst, wherein said olefin is functionalized by attachment of —CO—$YR^3$ groups wherein Y is O or S, and $R^3$ is H, hydrocarbyl, aryl, substituted aryl or substituted hydrocarbyl, and wherein the process is conducted in a pipe reactor containing static mixers to disperse gas into liquid for reaction, the process being operated in laminar flow.

9. The process of claim 8 wherein $R^3$ is hydrocarbyl and said olefin is functionalized to an ester.

10. The process of claim 1 wherein the acid catalyst comprises $BF_3$.

11. The process of claim 1 wherein $R^3$ is selected from aryl or substituted aryl and the recovered functionalized polymer is an ester.

12. The process of claim 1, wherein the polymeric olefin comprises polyalkene.

13. The process of claim 1, wherein the polymeric olefin comprises ethylene alpha-olefin copolymer having a number average molecular weight of from 500 to 10,000, wherein the copolymer is derived from ethylene and at least one alpha-olefin having the formula $H_2C=CHR^4$ wherein $R^4$ is straight chain or branched chain alkyl radical comprising 1 to 18 carbon atoms and wherein at least about 30% of the polymer chains possess terminal vinylidene unsaturation.

14. The process of claim 13, wherein the ethylene alpha-olefin copolymer comprises ethylene-butene-1 copolymer.

15. The process of claim 1, wherein $R^3$ is H or hydrocarbyl and at least about 50 mole percent of the functional groups —CO—Y—$R^3$ are attached to a tertiary carbon atom of the polymeric olefin backbone.

16. The process of claim 1, wherein $R^3$ is aryl, substituted aryl or substituted hydrocarbyl and at least 60 mole percent of the functional groups —CO—Y—$R^3$ are attached to a tertiary carbon atom of the polymeric olefin backbone.

17. The process of claim 8, wherein the process is operated in laminar flow with a Reynolds number of less than 10.

18. The process of claim 8, wherein the nucleophilic trapping agent has a pKa<12.

19. The process of claim 18, wherein the nucleophilic trapping agent comprises substituted phenol.

20. The process of claim 8, wherein the acid catalyst comprises $BF_3$.

21. The process of claim 8, wherein the olefin comprises polymeric olefin.

22. The process of claim 21, wherein the polymeric olefin comprises polyalkene.

23. The process of claim 21, wherein the nucleophilic trapping agent has a pKa<12.

24. The process of claim 23, wherein the nucleophilic trapping agent comprises substituted phenol.

25. The process of claim 21, wherein the acid catalyst comprises $BF_3$.

26. The process of claim 21, wherein the process is operated in laminar flow with a Reynolds number of less than 10.

27. The process of claim 8, wherein the dispersed gas is substantially composed of gas bubbles ranging in size from 0.01 to 3 mm.

28. The process of claim 14, wherein the olefin comprises polymeric olefin.

29. The process of claim 15, wherein the acid catalyst comprises $BF_3$.

* * * * *